United States Patent
Mais et al.

[11] Patent Number: 5,847,236
[45] Date of Patent: Dec. 8, 1998

[54] PROCESS FOR THE PREPARATION OF 2-CHLORO-4-METHYLPHENOL

[75] Inventors: Franz-Josef Mais, Düsseldorf; Helmut Fiege, Leverkusen, both of Germany

[73] Assignee: Bayer Aktiengesellschaft, Leverkusen, Germany

[21] Appl. No.: 710,990

[22] Filed: Sep. 25, 1996

[30]     Foreign Application Priority Data

Oct. 2, 1996 [DE] Germany ................ 195 36 846.0

[51] Int. Cl.⁶ .................................................. C07C 37/62
[52] U.S. Cl. ............................................. 568/779; 568/755
[58] Field of Search ................................ 568/755, 779

[56]             References Cited

U.S. PATENT DOCUMENTS

| | | |
|---|---|---|
| 2,494,993 | 1/1950 | Foster . |
| 3,920,757 | 11/1975 | Watson . |
| 4,429,168 | 1/1984 | Leston . |
| 4,876,396 | 10/1989 | LeBlanc et al. . |
| 5,149,858 | 9/1992 | Desmurs et al. . |

FOREIGN PATENT DOCUMENTS 2177396  1/1987  United Kingdom .

OTHER PUBLICATIONS

K–E. Bergquist, et al., Electrophilic Chlorination of 4–Methylphenols with Moelcular Chlorine. Synthesis of Dimethoxy Aromatics by Methanolysis of 4–Chloro–4–methylcyclohexa–2,5–dienones, Acata Chemica Scandinavica, B 36, pp. 675–683, (1982).

A. Fischer, et al., ipso Nitration. XXIX.[1] Nitration of substituted 4–methylanisoles and phenols, Can. J. Chem., vol. 65, pp. 1233–1240, (1987).

C.S. McClement, et al., The Rearrangement of ortho–Hydroxy–sulphones. Part VI., pp. 1016–1021. (1937).

W.D. Watson[1], Regioselective Para Chlorination of Activated Aromatic Compounds, J. Org. Chem., vol. 50, No. 12, pp. 2145–2148, (1985).

W.D. Watson, The Regioselective Para Chlorination of 2–Methylphenol, Tetrahedron Letters, No. 30, pp. 2591–2594, (1976).

Abstract of 174370u, Preparation of 3–chloro–2–hydroxy–5–nonyl benzophenone oxime, vol. 100, p. 591, (1984).

*Primary Examiner*—Gary Geist
*Assistant Examiner*—S. Padmanabhan
*Attorney, Agent, or Firm*—Sprung Kramer Schaefer & Briscoe

[57]             ABSTRACT

2-Chloro-4-methylphenol is prepared by reacting 4-methylphenol with a chlorinating agent in the presence of a catalyst system of one or more Lewis acids in a total amount of 0.1–10% by weight and one or more diaryl sulphides in a total amount of 0.1–10% by weight, all based on the amount of 4-methylphenol. The reaction temperature is 0°–100° C. The chlorinating agent is used in an amount of 0.5–1.5 mol per mole of 4-methylphenol. The reaction can be carried out until virtually complete consumption of the 4-methylphenol, high isomeric selectivity and high stage selectivity being observed.

20 Claims, No Drawings

PROCESS FOR THE PREPARATION OF 2-CHLORO-4-METHYLPHENOL

BACKGROUND OF THE INVENTION

1. Field of the Invention

The present invention relates to a process for the preparation of 2-chloro-4-methylphenol by reacting 4-methylphenol with a chlorinating agent in the presence of a catalyst system of Lewis acids and diaryl sulphides. In particular, the present invention relates to a process for the virtually complete highly selective chlorination of 4-methylphenol, avoiding complex work-up and purification operations.

2-Chloro-4-methylphenol is a valuable intermediate for the preparation of crop protection agents and pharmaceuticals.

2. Description of the Related Art

The chlorination of 4-methylphenol to give 2-chloro-4-methylphenol has long been known. In Acta Chem. Scand. B 36 (1982), 675, it is shown that in the various solvents mentioned there and in the presence of Lewis acids as catalysts, when, for example, 100 mol % of chlorine is used, a mixture of at least two monochlorinated products 2 and 3 is always formed:

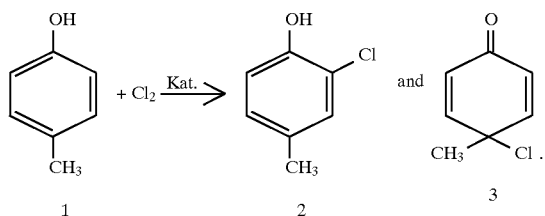

The product selectivity mentioned in general for the desired 2 is 60–80%, which is also confirmed by other literature (cf. Przem. Chem. 62 (1983) 605, cited in C.A., 100; (1984), 174370u; yield in chloroform there: 76%). The only exception to this selectivity range is given by the uncatalysed chlorination in $CS_2$ as solvent which gives a selectivity of up to 95%; however, $CS_2$ is not an industrially usable solvent because of the high flammability and the high toxicity. Chlorination of 4-methylphenol by chlorine without a solvent is further disclosed by U.S. Pat. No. 2,494,993 (Example 3 there). Double distillation is necessary for work-up and gives a product of low yield with questionable purity.

Unsatisfactory yields are also obtained according to the prior art when other chlorinating agents are used. For example, the chlorination of 4-methylphenol with $SO_2Cl_2$ is disclosed by Can. I. Chem. 65 (1987), 1233 or by J. Chem. Soc. 1937, 1016. After sometimes highly complex work-up, the yields are less than 60%.

Furthermore, catalysts are known which promote a selective ortho-chlorination of phenols, thus, for example, organic compounds of the elements of main groups V, VI and VII of the Periodic Table of the Elements (Mendeleev), or the addition of a primary, secondary or tertiary amine to the reaction mixture (U.S. Pat. No. 5,149,858 or U.S. Pat. No. 4,876,396). However, in this case, there is no example of, or else only a reference to, the chlorination of 4-methylphenol in the presence of the said additions. The promotion of chlorination of phenols in the para position to the OH group by chlorine or sulphuryl chloride in the presence of sulphur compounds and Lewis acids as catalyst system is also described (GB 2 177 396, U.S. Pat. No. 3,920,757, Tetrahedron Lett. 1976, 2591. J. Org. Chem. 50 (1985), 2145). Catalyst systems of this type accordingly suppress chlorination in the ortho position to the OH group. It was therefore not to be expected that sulphur compounds promote the chlorination of 4-methylphenol in the ortho position.

In addition to the selective chlorination in the ortho position to the OH group, the work-up of chlorination mixtures of 2-chloro-4-methylphenol with its unreacted starting product is also problematic. This is taught, for example, by U.S. Pat. No. 4,429,168. According to this, monochlorinated phenols can be separated off (eg. 2-chloro-4-methylphenol: b.p. 196° C. from its unchlorinated starting material 4-methylphenol having a very close boiling point: b.p.: 201.9° C.) by complexing with, for example, anhydrous calcium bromide (Example 13 in U.S. Pat. No. 4,429,168). This immense effort is industrially highly unfavourable. Our own studies have confirmed the general description in U.S. Pat. No. 4,429,168 and have shown that even small amounts of 4-methylphenol cannot practically be separated off by fractional distillation.

It was therefore further desirable to provide a simple reaction system of chlorination of 4-methylphenol to give 2-chloro-4-methylphenol. In particular, it was desirable to provide a process for the preparation of highly pure 2-chloro-4-methylphenol which does not require the complex work-up and purification operations.

SUMMARY OF THE INVENTION

A process has been found for the preparation of 2-chloro-4-methylphenol by reacting 4-methylphenol with a chlorinating agent in the presence of a Lewis acid, which is characterized in that the reaction is carried out at 0°–100° C. with 0.5–1.5 mol of chlorinating agent per mole of 4-methylphenol in the presence of a catalyst system of one or more Lewis acids in a total amount of 0.1–10% by weight and one or more diaryl sulphides in a total amount of 0.1–10% by weight, all based on the amount of 4-methylphenol.

DETAILED DESCRIPTION OF THE INVENTION

The starting material used for the process of the invention is conventional industrial 4-methylphenol. It is possible, and not further disadvantageous, that small traces of water are present in the 4-methylphenol. Preferably, technical grade 4-methylphenol is used having the conventional low water content which it contains in industry.

Chlorinating agents which are suitable are elemental chlorine or sulphuryl chloride or compounds which release these chlorinating agents. Preferably, elemental chlorine or sulphuryl chloride is used. The amount of chlorinating agent is 0.5–1.5 mol, preferably 0.8–1.2 mol, particularly preferably 0.9–1.15 mol, particularly preferably 0.95–1.1 mol, per mole of 4-methylphenol. It is an advantage here that the process of the invention produces an isomerically pure product, that is to say quinoid by-products, as indicated above, do not occur or do not occur in a detectable amount. The desired degree of purity of the 2-chloro-4-methylphenol can be set as a function of the molar amount of the chlorinating agent. Furthermore, it is advantageous and surprising that, in particular in the upper part of the molar amount of the chlorinating agent, even in the case of considerable conversion of the 4-methylphenol, no significant overchlorination occurs (high stage selectivity). This makes the difficult separation of the starting material 4-methylphenol from the reaction product 2-chloro-4-methylphenol unnecessary or simplifies it. In the process of the invention, therefore, chlorination is preferably carried out with an amount of 0.95–1.2 mol, preferably 0.98–1.15 mol, particularly preferably 1.0–1.1 mol, of chlorinating agent per mole of 4-methylphenol until the 4-methylphenol in the reaction mixture is virtually completely reacted, for example until its content in the reaction mixture is at most 1% by weight, preferably at most 0.5% by weight, particularly preferably at most 0.1% by weight, based on the weight of the 2-chloro-4-methylphenol formed. These maximum contents then represent the achievable purity of the 2-chloro-4-methylphenol obtained. Lewis acids for the process of the invention are those known to those skilled in the art, for example $AlCl_3$, $FeCl_3$, $SbCl_3$, $BF_3$, $ZnCl_2$, $FeBr_3$ and compounds from which the said substances can be formed, for example Al powder, Fe powder, $FeCl_2$ and others. In a preferred manner, $AlCl_3$, $FeCl_3$ or a precursor of the two, preferably preformed $AlCl_3$ or $FeCl_3$, is used. Obviously, a plurality can also be used, for example 2 or 3 of the said Lewis acids. The Lewis acid is used in an amount of 0.1–10% by weight, preferably 0.25–5% by weight, particularly preferably 0.5–2.5% by weight, based on the amount of 4-methylphenol.

Diaryl sulphides for use in the process of the invention are those of the formula

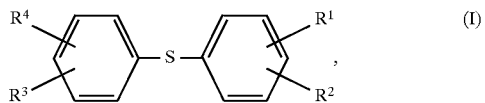

in which $R^1$, $R^2$, $R^3$ and $R^4$ independently of each other denote hydrogen, $C_1$–$C_4$-alkyl, $C_1$–$C_4$-alkoxy or halogen, preferably $R^1$ and $R^3$ independently of each other denote hydrogen, methyl, methoxy or chlorine and $R^2$ and $R^4$ denote hydrogen.

Diaryl sulphides of the formula (I) can accordingly be symmetrically or unsymmetrically substituted. $C_1$–$C_4$-Alkyl is, for example, methyl, ethyl, propyl, isopropyl, butyl or isobutyl. $C_1$–$C_4$-Alkoxy is, for example, methoxy, ethoxy, propoxy, isopropoxy, butoxy or isobutoxy. Halogen is fluorine, chlorine, bromine or iodine, preferably chlorine or bromine, particularly preferably chlorine. Important diaryl sulphides for the process of the invention are: unsubstituted diphenyl sulphide, 4,4'-dichloro-diphenyl sulphide or 4,4'-dimethyl-diphenyl sulphide. Similarly to the case of the Lewis acids, a mixture of a plurality of diaryl sulphides can also be used, for example 2 or 3. The amount of diaryl sulphide used is 0.1–10% by weight, preferably 0.25–5% by weight, particularly preferably 0.5–2.5% by weight, based on the amount of 4-methylphenol.

Within the scope of the said amounts for the Lewis acids and the diaryl sulphides, the two constituents of the catalyst system of the invention do not always need to be used in identical amounts. The molar ratio of Lewis acid to diaryl sulphide can rather be varied in a wide range and can be 0.1–10:1, preferably 0.25–5:1, particularly preferably 0.5–2:1.

The process of the invention is carried out at a temperature of 0°–100° C., preferably 0°–80° C., particularly preferably 10°–60° C., very particularly preferably 20°–40° C. The pressure over the reaction system of the process of the invention is not critical. Thus, atmospheric, slightly elevated or slightly reduced pressure can be employed. Elevated pressure can be indicated if the upper part of the temperature range is to be employed, using a low-boiling solvent; slightly reduced pressure can be indicated if, for temperature control, evaporative cooling, for example, is to be employed. In all other cases, for reasons of costs and to simplify the reaction apparatus, atmospheric pressure is employed.

The process of the invention is carried out in liquid phase. For this purpose, in the centre and upper part of the temperature range, it is sufficient to use molten starting product 4-methylphenol. However, it is equally possible to carry out the process in the presence of an inert solvent. Solvents of this type are known to those skilled in the art, for example methylene chloride, tetrachloroethane and perfluorohexane. Preferably, however, no solvent is employed.

The process of the invention can be carried out continuously, discontinuously or semi-continuously.

An exemplary embodiment of the process of the invention is as follows: 4-methylphenol is introduced as melt at a slightly elevated temperature into a chlorination reactor. After the catalyst mixture of Lewis acid and diaryl sulphide is added, the chlorinating agent is introduced in gaseous or liquid state in a uniform stream. When the desired content of 2-chloro-4-methylphenol is achieved, the chlorination is terminated. The salt-form portions produced from the Lewis acid are removed either by distillation of the volatile organic constituents or by aqueous washing of the entire product mixture. In both cases, organic phases containing the desired 2-chloro-4-methylphenol are obtained which are fractionated and purified by distillation. Obviously, fractionation and purification can also be performed by crystallization or chromatography. Work-up methods of this type are known to those skilled in the art.

The chlorination mixture is preferably worked up by distillation. Since a relatively long thermal stress of the catalyst-containing crude mixture could lead to the formation of by-products, the crude mixture is first subjected to a simple preliminary distillation, if appropriate in vacuo, leaving behind a small amount of residue, which essentially comprises the catalysts or their secondary products formed under the chlorination conditions. The catalyst-free crude distillate thus obtained is then subjected to a fractional distillation, if appropriate in vacuo. Since, according to the invention, it is not necessary to separate off the 4-methylphenol (lower purity sufficient or further chlorination of the invention possible), only a low separation efficiency is necessary in this fractional distillation to separate off higher-boiling by-products. In a very simple manner and in high yield, a 2-chloro-4-methylphenol is thus obtained which contains as sole significant impurity 4-methylphenol, whose amount is determined according to the invention by the amount of chlorinating agent used.

The yields of 2-chloro-4-methylphenol to be achieved using the catalyst system of the invention are greater than 90%, based on 4-methylphenol; the product selectivities for 2-chloro-4-methylphenol are generally greater than 93%, frequently greater than 96%. Such an increase in selectivity in comparison with processes of the prior art was not to be expected and is extremely surprising. This is all the more so, since according to the prior art, it was to be expected that a catalyst system containing a sulphur compound should suppress a chlorination in the ortho position to the OH group. According to the invention, the exact opposite is achieved, that is an extremely intense increase in selectivity to give the 2-chloro-4-methylphenol. It is further surprising that the high isomeric selectivity described is maintained up to virtually complete conversion of the 4-methylphenol. A further interesting and surprising result is also the high stage selectivity, even at very high conversion of 4-methylphenol, as a result of which polychlorinated species occur only in traces and the work-up is simplified in the described manner.

EXAMPLES

Example 1

100 parts by weight of 4-methylphenol were introduced molten into a chlorination beaker protected from light at 36°–37° C. and 1.0 part by weight of $AlCl_3$ and 1.0 part by weight of diphenyl sulphide were added. The reaction batch was then brought to 31°–32° C. with slight cooling and 70.5 parts by weight of chlorine were introduced in the course of approximately 4 h at 25°–30° C. at a uniform rate. The product mixture obtained was analysed by calibrated gas chromatography. The mixture contained 1.8% of 4-methylphenol, 94.7% of 2-chloro-4-methylphenol and 3.5% of unknown substances. This corresponds to a selectivity of formation for 2-chloro-4-methylphenol of 96.4%.

Example 2

Example 1 was repeated, but instead of AlCl$_3$, 1.0 part by weight of FeCl$_3$ was used. According to GC analysis, a chlorination mixture of 1.6% of 4-methylphenol, 94.5% of 2-chloro-4-methylphenol and 3.9% of unknown substances was obtained. This corresponds to a selectivity of formation of 96.0%.

Example 3

100 parts by weight of 4-methylphenol were introduced molten at 36°–40° C. into a stirred vessel and 1.0 part by weight of AlCl$_3$ and 1.0 part by weight of diphenyl sulphide were added. The mixture was cooled to approximately 30° C. and 135 parts by weight of sulphuryl chloride were added at 28°–30° C. in the course of 1 h. After a further stirring time of 1 h at approximately 25° C., the reaction mixture was analysed by calibrated GC analysis as in Example 1. A mixture of 0.95% of 4-methylphenol, 95.81% of 2-chlorophenol and 3.24% of unknown substances was obtained. This corresponds to a selectivity of formation of 96.73%.

Example 4

Example 3 was repeated using 0.5 part by weight of AlCl$_3$ and 0.5 part by weight of diphenyl sulphide and at a chlorination temperature of 23°–25° C. A chlorination mixture containing 1.1% of 4-methylphenol, 92.2% of 2-chloro-4-methylphenol and 6.7% of unknown substances was obtained. The selectivity of formation for 2-chloro-4-methylphenol was thus 93.23%.

Example 5

Example 3 was repeated using 1.0 part by weight of FeCl$_3$ instead of AlCl$_3$ and at a chlorination temperature of 23°–25° C. A chlorination mixture containing 0.90% of 4-methylphenol, 94.91% of 2-chloro-4-methylphenol and 4.19% of unknown substances was obtained. This gave a selectivity of formation for 2-chloro-4-methylphenol of 95.77%.

Example 6

The process of Example 1 was repeated, but instead of AlCl$_3$, 2.5 parts by weight of FeCl$_3$ and 69.5 parts by weight of chlorine were used at 25°–27° C. At a residual content of 2.2% of 4-methylphenol, a selectivity of formation for 2-chloro-4-methylphenol of 94.6% was achieved.

Example 7

The process of Example 1 was repeated using 1.5 parts by weight of AlCl$_3$ instead of 1.0 part by weight of AlCl$_3$ at a chlorination temperature of 23°–25° C. and using 71.0 parts by weight of chlorine. At a residual content of 0.90% of 4-methylphenol, a selectivity of formation resulted for 2-chloro-4-methylphenol of 94.9%.

Example 8

The process of Example 1 was repeated, except that 1.2 parts by weight of 4,4'-dichloro-diphenyl sulphide were used instead of diphenyl sulphide. A residue content of 1.05% of 4-methylphenol and a selectivity of formation for 2-chloro-4-methylphenol of 95.9% were found by GC analysis.

Example 9

The process of Example 1 was repeated using 1.1 parts by weight of 4,4'-dimethyl-diphenyl sulphide. A content of 4-methylphenol of 1.35% and of 2-chloro- 4-methylphenol of 94.9% was found by GC analysis. This gives a selectivity of formation of 96.2%.

Example 10

100 parts by weight of 4-methylphenol were melted at 35°–37° C. and introduced with stirring. To this were added in succession 1 part by weight of AlCl$_3$ and 1 part by weight of diphenyl sulphide and, initially at 32°–33° C., later at 20°–25° C., 125 parts by weight of sulphuryl chloride were introduced in the course of 2 h at a uniform rate. The mixture was then stirred for a further 1 h at 23°–25° C. 146 parts by weight of chlorination mixture were obtained which contained, according to calibrated gas-chromatographic analysis, 0.65% of 4-methylphenol and 96.25% of 2-chloro-4-methylphenol. The product was distilled in vacuo at 50 mbar. A colourless, water-clear crude distillate of 140.5 parts by weight and a residue of 5 parts by weight were obtained. Fine distillation of the crude distillate at 100 mbar gave, without drawing off first runnings, a single fraction of 131 parts by weight having a content (calibrated GC) of 0.70% of 4-methylphenol and of 99.26% of 2-chloro-4-methylphenol (0.04% unknown).

Examples 11–18

The chlorination of Example 10 was repeated using chlorine or sulphuryl chloride as chlorinating agent, employing various catalysts of the invention. The results are given in the following table. 100 parts by weight of 4-methylphenol were used each time. The amount of chlorinating agent was 1 to 1.1 mol per mole of 4-methylphenol.

| Ex.-No. | Chlorinating agents | Amounts added parts by weight | Cat. I | Amount of cat. I parts by weight | Cat. II | Amount of cat. II parts by weight | Chlorination time [h] | Temperature [°C.] Initially | Temperature [°C.] Later | Chlorination mixture parts by weight | GC composition 4-methyl-phenol | GC composition 2-Chloro-4-methyl-phenol |
|---|---|---|---|---|---|---|---|---|---|---|---|---|
| 11 | Cl$_2$ | 73.8 | FeCl$_3$ | 1.5 | Ph$_2$S | 1.0 | 4 | 31–33 | 22–24 | 145.9 | 0.02 | 93.02 |
| 12 | Cl$_2$ | 73.3 | AlCl$_3$ | 1.0 | Ph$_2$S | 1.0 | 4 | 32–33 | 22–25 | 145.1 | 0.03 | 93.65 |
| 13 | Cl$_2$ | 71.0 | AlCl$_3$ | 1.5 | Ph$_2$S | 1.0 | 4, 5 | 31–32 | 22–24 | 143.2 | 0.66 | 96.30 |
| 14 | SO$_2$Cl$_2$ | 135.0 | FeCl$_3$ | 1.0 | Ph$_2$S | 1.0 | 2 | 30–31 | 24–26 | 143.8 | 0.90 | 94.91 |
| 15 | SO$_2$Cl$_2$ | 135.0 | AlCl$_3$ | 0.5 | Ph$_2$S | 0.5 | 2 | 31–32 | 23–25 | 142.0 | 1.10 | 92.20 |

| Ex.-No. | Chlori-nating agents | Amounts added parts by weight Cat. I | Amount of cat. I parts by weight | Cat. II | Amount of cat. II parts by weight | Chlori-nation time [h] | Temperature [°C.] Initially | Temperature [°C.] Later | Chlori-nation mixture parts by weight | GC composition 4-methyl-phenol | GC composition 2-Chloro-4-methyl-phenol |
|---|---|---|---|---|---|---|---|---|---|---|---|
| 16 | Cl$_2$ | 73.6 | 1.0 | AlCl$_3$ [Cl—⟨C$_6$H$_4$⟩—]$_2$S | 1.2 | 4 | 32–33 | 24–26 | 145.8 | 0.04 | 93.50 |
| 17 | Cl$_2$ | 73.4 | 1.0 | AlCl$_3$ [Me—⟨C$_6$H$_4$⟩—]$_2$S | 1.1 | 4 | 31–32 | 24–26 | 144.9 | 0.07 | 93.70 |
| 18 | Cl$_2$ | 78.1 | 1.5 | AlCl$_3$ Ph$_2$S | 1.0 | 6 | 31–32 | 20–23 | 150.2 | 0.00 | 88.52 |

Example 19

Preparation of 2-chloro-4-methylphenol having a residual content of less than 0.5% 4-methylphenol.

100 parts by weight of 4-methylphenol were melted at 35°–36° C. and stirred. 0.96% by weight of AlCl$_3$ and 1.0 part by weight of diphenyl sulphide were added and 73.1 parts by weight of chlorine were introduced uniformly in the course of 4 h at initially 32°–33° C., later 22°–25° C. After a further stirring phase of 1 h at 24°–25° C., a chlorination mixture of 145.5 parts by weight was obtained having a GC content of 0.46% of 4-methylphenol and 93.16% of 2-chloro-4-methylphenol. Work-up by distillation analogously to Example 10 produced 130.3 parts by weight of pure product of composition 0.49% of 4-methylphenol, 99.47% of 2-chloro-4-methylphenol and 0.04% of unknown.

Example 20

Preparation of 2-chloro-4-methylphenol having a residual content of less than 0.05% 4-methylphenol.

100 parts by weight of 4-methylphenol were melted at ~35° C. and stirred. To this were added 1.5 parts by weight of AlCl$_3$ and 0.95 part by weight of diphenyl sulphide. 74.6 parts by weight of gaseous chlorine were introduced uniformly in the course of 6 h, initially at 30°–31° C., later at 22°–25° C. After a short further stirring phase at approximately 25° C., 146.2 parts by weight of crude product were obtained of the GC composition 0.03% of 4-methylphenol and 93.20% of 2-chloro-4-methylphenol. Work-up by distillation produced 127.8 parts by weight of pure distillate having a GC content of 0.03% of 4-methylphenol, 99.92% of 2-chloro-4-methylphenol and 0.05% of unknown.

What is claimed is:

1. A process for the preparation of 2-chloro-4-methylphenol in yields of 90% or greater by reacting 4-methylphenol with a chlorinating agent in the presence of a Lewis acid, wherein the reaction is carried out at 0°–100° C. with 0.5–1.5 mol of chlorinating agent per mole of 4-methylphenol in the presence of a catalyst system of one or more Lewis acids in a total amount of 0.1–10% by weight and one or more diaryl sulphides in a total amount of 0.1–10% by weight, all based on the amount of 4-methylphenol.

2. The process of claim 1, wherein the chlorination agent used is chlorine or sulphuryl chloride.

3. The process of claim 1, wherein the chlorinating agent is used in an amount of 0.8–1.2 mol per mol of 4-methylphenol.

4. The process of claim 3, wherein the chlorinating agent is used in an amount of 0.9–1.15 mol per mol of 4-methylphenol.

5. The process of claim 4, wherein the chlorinating agent is used in an amount of 0.95–1.1 mol per mol of 4-methylphenol.

6. The process of claim 1, wherein the chlorination is carried out using an amount of 0.95–1.2 mol of chlorinating agent per mol of 4-methylphenol until the content of 4-methylphenol in the reaction mixture is at most 1% by weight, based on the weight of 2-chloro-4-methylphenol formed.

7. The process of claim 6, wherein the chlorination is carried out using an amount of 0.98–1.15 mol of chlorinating agent per mol of 4-methylphenol until the content of 4-methylphenol is at most 1% by weight, based on the weight of 2-chloro-4-methylphenol formed.

8. The process of claim 7, wherein the chlorination is carried out using an amount of 1.0–1.1 mol of chlorinating agent per mol of 4-methylphenol until the content of 4-methylphenol is at most 1% by weight, based on the weight of 2-chloro-4-methylphenol formed.

9. The process of claim 1, wherein the Lewis acid used is AlCl$_3$, FeCl$_3$ or precursors of AlCl$_3$ or FeCl$_3$.

10. The process of claim 9, wherein the Lewis acid used is AlCl$_3$ or FeCl$_3$.

11. The process of claim 1, wherein the Lewis acid is used in an amount of 0.25–5% by weight, based on the amount of 4-methylphenol.

12. The process of claim 11, wherein the Lewis acid is used in an amount of 0.5–2.5% by weight, based on the amount of 4-methylphenol.

13. The process of claim 1, wherein a diaryl sulphide of the formula

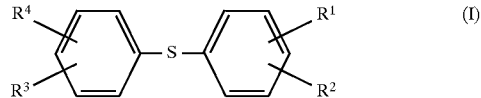

is used, in which

R$^1$, R$^2$, R$^3$ and R$^4$ independently of each other denote hydrogen, C$_1$–C$_4$-alkyl, C$_1$–C$_4$-alkoxy or halogen.

14. The process of claim 13, wherein R$^1$ and R$^3$ independently of each other denote hydrogen, methyl or chlorine and R$^2$ and R$^4$ denote hydrogen.

15. The process of claim 1, wherein the diaryl sulphide is used in an amount of 0.25–5% by weight, based on the amount of 4-methylphenol.

16. The process of claim 15, wherein the diaryl sulphide is used in an amount of 0.5–2.5% by weight, based on the amount of 4-methylphenol.

17. The process of claim 1, wherein the molar ratio of Lewis acid to diaryl sulphide is 0.1–10:1.

18. The process of claim 17, wherein the molar ratio of Lewis acid to diaryl sulphide is 0.25–5:1.

19. The process of claim 1, wherein the reaction is carried out at a temperature of 0°–80° C.

20. The process of claim 19, wherein the reaction is carried out at a temperature of 10°–60° C.

* * * * *

UNITED STATES PATENT AND TRADEMARK OFFICE
CERTIFICATE OF CORRECTION

PATENT NO. : 5,847,236
DATED      : Dec.8,1998
INVENTOR(S): Mais, et al.

It is certified that error appears in the above-identified patent and that said Letters Patent is hereby corrected as shown below:

On the title page, Item [30], after "Oct.2," delete "1996" and insert --1995--.

Signed and Sealed this

Sixth Day of July, 1999

Attest:

Q. TODD DICKINSON

*Attesting Officer*    Acting Commissioner of Patents and Trademarks